US005847267A

United States Patent [19]

Janzen

[11] Patent Number: 5,847,267

[45] Date of Patent: Dec. 8, 1998

[54] PROCESS TO OBTAIN DYNAMIC SHEAR MODULUS COMPONENTS OF A POLYMER BY USING STEADY-STATE-FLOW DATA

[75] Inventor: Jay Janzen, Bartlesville, Okla.

[73] Assignee: Phillips Petroleum Company, Bartlesville, Okla.

[21] Appl. No.: 880,034

[22] Filed: Jun. 20, 1997

[51] Int. Cl.[6] .......... G01N 11/00

[52] U.S. Cl. .......... 73/54.01

[58] Field of Search .......... 73/54.01, 54.04, 73/54.09, 54.11, 54.14, 54.05, 54.06

[56] References Cited

U.S. PATENT DOCUMENTS

| | | | |
|---|---|---|---|
| 4,027,526 | 6/1977 | Osmers | 73/54.01 |
| 4,154,093 | 5/1979 | Smith et al. | 73/54.01 |
| 4,165,634 | 8/1979 | Prevorsek et al. | 73/810 |
| 4,241,602 | 12/1980 | Han et al. | 73/56 |
| 4,754,640 | 7/1988 | Fitzgerald et al. | 73/54 |
| 4,754,645 | 7/1988 | Piche et al. | 73/54.01 |
| 4,794,788 | 1/1989 | Masters | 73/54.27 |
| 4,798,081 | 1/1989 | Hazlitt et al. | 73/53.01 |
| 4,992,487 | 2/1991 | Rao | 73/54.01 |
| 5,081,870 | 1/1992 | Fitzgerald | 73/575 |
| 5,103,679 | 4/1992 | Porter et al. | 78/843 |
| 5,543,477 | 8/1996 | Latiolais et al. | 526/65 |

*Primary Examiner*—Hezron Williams
*Assistant Examiner*—Jay L. Politzer
*Attorney, Agent, or Firm*—Carl D. Corvin

[57] ABSTRACT

A process to obtain the shear storage modulus G'(ω) and/or the shear loss modulus G"(ω) of a polymer is provided. This process comprises: (a) producing a viscosity data set by measuring the viscosity of said polymer at various shear rates, while said polymer is in a melted state; (b) producing a parameter data set that comprises values for $\eta_0$, $\tau_\eta$ and $\alpha$ by analyzing said viscosity data set; and (c) obtaining said shear storage modulus G'(ω) and the shear loss modulus G"(ω) by using said parameter data set.

15 Claims, No Drawings

PROCESS TO OBTAIN DYNAMIC SHEAR MODULUS COMPONENTS OF A POLYMER BY USING STEADY-STATE-FLOW DATA

FIELD OF THE INVENTION

This invention is related to the field of polymers.

BACKGROUND OF THE INVENTION

Capillary rheometers are used to monitor polymer production. Since capillary rheometers have a sturdy design they are often used in on-line applications to provide information about the polymer being produced. In general, these capillary rheometers provide viscosity data based on the steady-state-flow behavior of the polymer. However, polymers have significant viscoelastic properties that contribute to their non-Newtonian flow behavior. Information concerning these viscoelastic properties is not easy to obtain from capillary rheometers.

One approach has been to generate a dynamic flow deformation in an on-line capillary rheometer. This is accomplished by modulating the speed control on a gear pump to produce a sinusoidal flow deformation and by modifying the capillary rheometer. However, this approach is unsatisfactory because it is not very accurate and the equipment is more susceptible to mechanical breakdown.

Consequently, the inventor provides this invention so that information concerning such viscoelastic properties can be obtained economically and accurately.

SUMMARY OF THE INVENTION

It is an object of this invention to provide a process to obtain the shear storage modulus $G'(\omega)$ of a polymer.

It is another object of this invention to provide a process to obtain the shear loss modulus $G''(\omega)$ of a polymer.

It is yet another object of this invention to provide a process to obtain the shear storage modulus $G'(\omega)$ and the shear loss modulus $G''\omega)$ of a polymer.

In accordance with this invention a process to obtain the shear storage modulus $G'(\omega)$ of a polymer is provided. This process comprises:

(a) producing a viscosity data set by measuring the viscosity of said polymer at various shear rates, while said polymer is in a melted condition;

(b) producing a parameter data set that comprises values for $\eta_0$, $\tau_\eta$, and $\alpha$, by analyzing said viscosity data set; and (c) obtaining said shear storage modulus $G'(\omega)$ by using said parameter data set.

In accordance with this invention a process to obtain the shear loss modulus $G''\omega)$ of a polymer is provided. This process comprises:

(a) producing a viscosity data set by measuring the viscosity of said polymer at various shear rates, while said polymer is in a melted condition;

(b) producing a parameter data set that comprises values for $\eta_0$, $\tau_\eta$ and $\alpha$ by analyzing said viscosity data set; and (c) obtaining said shear loss modulus $G''(\omega)$ by using said parameter data set.

In accordance with this invention a process to obtain the shear storage modulus $G'(\omega)$ and the shear loss modulus $G''(\omega)$ of a polymer is provided. This process comprises:

(a) producing a viscosity data set by measuring the viscosity of said polymer at various shear rates, while said polymer is in a melted condition;

(b) producing a parameter data set that comprises values for $\eta_0$, $\tau_\eta$ and $\alpha$ by analyzing said viscosity data set; and (c) obtaining said shear storage modulus $G'(\omega)$ and the shear loss modulus $G''\omega)$ by using said parameter data set.

The advantages and usefulness of this invention will become more apparent from the following.

DETAILED DESCRIPTION OF THE INVENTION

The shear storage modulus $G'(\omega)$ and the shear loss modulus $G''(\omega)$ of a polymer provide important information concerning the viscoelastic properties of such polymer. This invention provides a process to obtain this information. This information is obtained from the polymer by using data obtained from the polymer while said polymer is in a melted condition.

The simplified[1] form of the Carreau-Yasuda non-Newtonian viscosity model which can be used for fitting isothermal viscosity data is $$\eta(\dot{\gamma})=\eta_0[1+(\tau_\eta\dot{\gamma})^\alpha]^{(n-1)/\alpha} \quad (1a)$$

where $\eta(\dot{\gamma})$ is the shear rate-dependent viscosity, $\eta_0$ is its low-rate limiting value, called the zero-shear viscosity, $\dot{\gamma}$ is the shear rate, $\tau_\eta$ is a characteristic viscous relaxation time, $\alpha$ is a parameter inversely related to the breadth of the transition from Newtonian to power-law behavior, and n fixes the final slope (the limiting power-law behavior of the viscosity at large $\dot{\gamma}$). Equation 1a is for application at shear rates short of where wall slip occurs.

[1] R. Byron Bird, Robert C. Armstrong, and Ole Hassager, *Dynamics of Polymeric Liquids*, 2nd ed. (John Wiley & Sons, New York, 1987).

If the empirical Cox-Merz[2] rule holds, the analogous form $$|\eta^*(\omega)|=\eta_0[1+(\tau_\eta\omega)^\alpha]^{(n-1)/\alpha} \quad (1b)$$

will (with the same values of the parameters $\eta_0$, $\tau_\eta$, and $\alpha$) simultaneously represent complex viscosity data for the same material at the same temperature. Here $|\eta^*(\omega)|$ is the scalar magnitude of the complex viscosity[3] $\eta^*(\omega)$, and $\omega$ is the angular frequency of an oscillatory shearing deformation. $\eta^*(\omega)$ is convertible into $G^*(\omega)$ via the identity $$G^*(\omega)=i\omega\eta^*(\omega)$$

[2] W. P. Cox and E. H. Merz, "Correlation of Dynamic and Steady Flow Viscosities", J. Polym. Sci. 28, 619–622 (1958).

[3] John M. Dealy, "Official Nomenclature for Material Functions Describing the Response of a Viscoelastic Fluid to Various Shearing and Extensional Deformations", J. Rheol. 39, 253–265 (1995).

The technique used to obtain the results to be further utilized below is quite straightforward in its nonlinear least-squares fitting and parameter estimation aspects.

Data are routinely acquired from capillary rheometers in the form of tables of shear rates and the corresponding viscosities. Such tables are easily loaded into graphics programs for analysis. Then logarithms are taken to obtain the data points $(x_j, y_j)$ for curve fitting:

$$x_j=\log\dot{\gamma}_j;$$

$$y_j=\log\eta(\dot{\gamma}_j)$$

Finally, the program is given some initial values for[4] $\eta_0$, $\tau_\eta$, and $\alpha$ and then the program adjusts them so as to minimize the weighted sum of squared residuals $$\sum_{j=1}^{m} w_j (y_j - Y_j)^2$$

where the calculated ordinate $Y_j$ is the logarithm of the expression on the right-hand side of (1a), and the statistical weights $w_j$ are taken equal to 1 if the $x_j$'s are evenly spaced; otherwise we use $$w_1 \alpha x_2 - x_1,$$

$$w_m \alpha x_m - x_{m-1},$$

and $$w_j \alpha (x_{j+1} - x_{j-1})/2 \text{ for } j=2, \ldots, m-1$$

for the reason that such weights enforce effectively equal spacing. That is, they keep closely-spaced clusters of data points from having an unduly large influence on the outcome of the least-squares parameter estimation, that is, on the over-all shape of the fitted curve.

[4] Suitable values would be:

$\eta_0 \approx \max[\eta(\dot{\gamma})] = \eta(\dot{\gamma}_{min})$;

$\tau_\eta \approx \eta_0/10^5$;

$\alpha \approx 0.3$.

The results obtained are a set of values for the three parameters $\eta_0$, $\tau_\eta$, and $\alpha$. (Because practical experiments seldom yield data covering a wide enough range of shear rates to contain significant information about the value of n, it is usually necessary to take n as a fixed constant; we use the value 2/11 suggested by Graessley[5,6] on theoretical grounds).

[5] W. W. Graessley, "Viscosity of Entangling Polydisperse Polymers", J. Chem Phys. 47, 1942–1953 (1967).

[6] William W. Graessley, "The Entanglement Concept in Polymer Rheology", Adv. Polym. Sci. 16, 1–176 (1974).

With $\eta_0$, $\tau_\eta$, and $\alpha$ having been determined, it is now possible to obtain good approximations to the storage (G') and loss (G") components of the complex shear modulus $$G^*(\omega) \equiv G'(\omega) + iG''(\omega)$$

by use of the following equations:

$$G'(\omega) \approx \eta_0 \omega \left[1 + (\tau_\eta \omega)^a\right]^{(n-1)/a} \cos\left[\frac{\pi}{2}\left(\frac{1 + n(\omega\tau_\eta)^a}{1 + (\omega\tau_\eta)^a}\right)\right] \quad (2)$$

and $$G''(\omega) \approx \eta_0 \omega \left[1 + (\tau_\eta \omega)^a\right]^{(n-1)/a} \sin\left[\frac{\pi}{2}\left(\frac{1 + n(\omega\tau_\eta)^a}{1 + (\omega\tau_\eta)^a}\right)\right] \quad (3)$$

The first step in this invention is to produce a viscosity data set by measuring the isothermal viscosity of a polymer at various shear rates. This step can be accomplished by a person with ordinary skill in the art. Currently, the preferred method is to use a capillary rheometer to provide such viscosity data set. Capillary rheometers are well known in the art. The viscosity data set should include enough information to adequately describe the viscosity as a function of the shear rate for such polymer. Usually, this viscosity data set is in the form of a table of shear rates and corresponding viscosities for a fixed temperature.

The second step in this invention is to produce a parameter data set that comprises values for "$\eta_0$, $\tau_\eta$, and $\alpha$" by analyzing said viscosity data set. This step can also be accomplished by a person with ordinary skill in the art. There are various programs known in the art that can obtain values for this parameter data set. In particular, KaleidaGraph[7] or SigmaPlot[8] can be used to produce the desired parameter set. These programs use a non-linear least squares approach to determine the values for the parameter data set. That is, the program adjusts the values for the parameter data set to minimize the weighted sum of the squared residuals.

[7] Available from Synergy Software (PCS Inc.) 2457 Perkiomen Avenue, Reading, Pa. 19606.

[8] Available from Jandel Scientific, 65 Koch Road, Corte Madera, Calif. 94925.

The third step in this invention is to obtain said shear storage modulus G'(ω) and the shear loss modulus G"(ω) by using said parameter data set. This can be done by using equations (2) and (3).

$$G'(\omega) \approx \frac{\eta_0 \omega}{\left[1 + (\tau_\eta \omega)^a\right]^{(1-n)/a}} \cdot \cos\left[\frac{\pi}{2}\left(\frac{(1 + n(\omega\tau_\eta)^a)}{(1 + (\omega\tau_\eta)^a)}\right)\right] \quad (2)$$

$$G''(\omega) \approx \frac{\eta_0 \omega}{\left[1 + (\tau_\eta \omega)^a\right]^{(1-n)/a}} \cdot \sin\left[\frac{\pi}{2}\left(\frac{(1 + n(\omega\tau_\eta)^a)}{(1 + (\omega\tau_\eta)^a)}\right)\right] \quad (3)$$

In general, this process can be used for a wide variety of polymer such as, for example, polyethylene, polypropylene, poly(4-methyl-1-pentene), poly(3-ethyl-1-hexene), polystyrene, polyphenylene sulfide, polycarbonates, and polybutadiene.

That which is claimed is:

1. A process to obtain the shear storage modulus G'(ω) of a polymer said process comprising:

(a) producing a viscosity data set by measuring the viscosity of said polymer at various shear rates, while said polymer is in a melted condition;

(b) producing a parameter data set that comprises values for $\eta_0$, $\tau_\eta$, and $\alpha$, by analyzing said viscosity data set; and (c) obtaining said shear storage modulus G'(ω) by using said parameter data set.

2. A process according to claim 1 wherein said viscosity data set is produced using a capillary rheometer.

3. A process according to claim 2 wherein said parameter data set consists essentially of values for $\eta_0$, $\tau_\eta$, and $\alpha$.

4. A process according to claim 3 wherein said parameter data set consists of values for $\eta_0$, $\tau_\eta$, and $\alpha$.

5. A process according to claim 4 wherein said shear storage modulus G'(ω) is obtained by using said parameter data set in conjunction with equation (2)

$$G'(\omega) \approx \frac{\eta_0 \omega}{\left[1 + (\tau_\eta \omega)^a\right]^{(1-n)/a}} \cdot \cos\left[\frac{\pi}{2}\left(\frac{(1 + n(\omega\tau_\eta)^a)}{(1 + (\omega\tau_\eta)^a)}\right)\right] \quad (2)$$

6. A process to obtain the shear loss modulus G"(ω) of a polymer said process comprising:

(a) producing a viscosity data set by measuring the viscosity of said polymer at various shear rates, while said polymer is in a melted condition;

(b) producing a parameter data set that comprises values for $\eta_0$, $\tau_\eta$ and $\alpha$ by analyzing said viscosity data set;

(c) obtaining said shear loss modulus G"(ω) by using said parameter data set.

7. A process according to claim 6 wherein said viscosity data set is produced using a capillary rheometer.

8. A process according to claim 7 wherein said parameter data set consists essentially of values for $\eta_0$, $\tau_\eta$, and $\alpha$.

9. A process according to claim 8 wherein said parameter data set consists of values for $\eta_0$, $\tau_\eta$, and $\alpha$.

10. A process according to claim 9 wherein said shear storage modulus G"(ω) is obtained by using said parameter data set in conjunction with equation (3)

$$G''(\omega) \approx \frac{\eta_0\omega}{[1+(\tau_\eta\omega)^a]^{(1-n)/a}} \cdot \sin\left[\frac{\pi}{2}\left(\frac{(1+n\,(\omega\tau_\eta)^a)}{(1+(\omega\tau_\eta)^a)}\right)\right] \quad (3)$$

11. A process to obtain the shear storage modulus G'(ω) and the shear loss modulus G"(ω) of a polymer said process comprising:

(a) producing a viscosity data set by measuring the viscosity of said polymer at various shear rates, while said polymer is in a melted condition;

(b) producing a parameter data set that comprises values for $\eta_0$, $\tau_\eta$ and α by analyzing said viscosity data set; and (c) obtaining said shear storage modulus G'(ω) and the shear loss modulus G"(ω) by using said parameter data set.

12. A process according to claim 11 wherein said viscosity data set is produced using a capillary rheometer.

13. A process according to claim 12 wherein said parameter data set consists essentially of values for $\eta_0$, $\tau_\eta$, and α.

14. A process according to claim 13 wherein said parameter data set consists of values for $\eta_0$, $\tau_\eta$, and α.

15. A process according to claim 14 wherein said shear storage modulus G'(ω) and G"(ω) is obtained by using said parameter data set in conjunction with equations (2) and (3)

$$G'(\omega) \approx \frac{\eta_0\omega}{[1+(\tau_\eta\omega)^a]^{(1-n)/a}} \cdot \cos\left[\frac{\pi}{2}\left(\frac{(1+n\,(\omega\tau_\eta)^a)}{(1+(\omega\tau_\eta)^a)}\right)\right] \quad (2)$$

$$G''(\omega) \approx \frac{\eta_0\omega}{[1+(\tau_\eta\omega)^a]^{(1-n)/a}} \cdot \sin\left[\frac{\pi}{2}\left(\frac{(1+n\,(\omega\tau_\eta)^a)}{(1+(\omega\tau_\eta)^a)}\right)\right] \quad (3)$$

* * * * *